(12) United States Patent
Zheng

(10) Patent No.: US 7,985,408 B2
(45) Date of Patent: Jul. 26, 2011

(54) TENOCYTE CELL CULTURING METHOD

(75) Inventor: Ming Hao Zheng, City Beach (AU)

(73) Assignee: The University of Western Australia, Nedlands (AU)

( * ) Notice: Subject to any disclaimer, the term of this patent is extended or adjusted under 35 U.S.C. 154(b) by 72 days.

(21) Appl. No.: 12/294,169

(22) PCT Filed: Mar. 23, 2007

(86) PCT No.: PCT/AU2007/000362
§ 371 (c)(1),
(2), (4) Date: Mar. 19, 2009

(87) PCT Pub. No.: WO2007/106949
PCT Pub. Date: Sep. 27, 2007

(65) Prior Publication Data
US 2009/0191161 A1    Jul. 30, 2009

(30) Foreign Application Priority Data
Mar. 23, 2006   (AU) .............................. 2006901495

(51) Int. Cl.
*A01N 63/00*   (2006.01)
*C12N 5/00*   (2006.01)
*C12N 5/02*   (2006.01)

(52) U.S. Cl. ........ 424/93.7; 435/379; 435/383; 435/404

(58) Field of Classification Search .................. None
See application file for complete search history.

(56) References Cited

U.S. PATENT DOCUMENTS

| | | | |
|---|---|---|---|
| 4,939,239 A | 7/1990 | Matsuhashi et al. | |
| 6,368,298 B1 | 4/2002 | Beretta et al. | |
| 6,569,172 B2 | 5/2003 | Asculai et al. | |
| 2002/0173806 A1 | 11/2002 | Gianetti et al. | |
| 2003/0144197 A1 | 7/2003 | Zheng et al. | |
| 2004/0037812 A1 | 2/2004 | Giannetti | |
| 2004/0078077 A1 | 4/2004 | Binette et al. | |
| 2004/0267362 A1 | 12/2004 | Hwang et al. | |
| 2005/0177249 A1 | 8/2005 | Kladaki et al. | |
| 2005/0226856 A1 | 10/2005 | Ahlfors | |

OTHER PUBLICATIONS

Abrahamsson, S.O. et al., "Differential Effects of Insulin-Like Growth Factor-I on Matrix and DNA Synthesis in Various Regions and Types of Rabbit Tendons," J. Ortho. Res., 1996, 14, 370-376.
Abrahamsson, S.O.J., "Similar Effects of Recombinant Human Insulin-Like Growth Factor-I and II on Cellular Activities in Flexor-Tendons of Young Rabbits: Experimental Studies in Vitro," Ortho. Res., 1996, 15, 256-262.
Abrahamsson, S.O. et al., "Recombinant human insulin-like growth factor-1 stimulates in vitro matrix synthesis and cell proliferation in rabbit flexor tendon," Journal of Orthopaedic Research, 1991, 9(4), 495-502.
Abrahamsson, S.O. et al., "Long-Term Explant Culture of Rabbit Flexor Tendon: Effects of Recombinant Human Insulin-Like Growth factor-I and Serum on Matrix Metabolism," Journal of Orthopaedic Research, 1991, 9, 503-515.

Anitua, E. et al., "Autologous preparations rich in growth factors promote proliferation and induce VEGF and HGF production by human tendon cells in culture," J. Ortho Res., 2005, 23, 281-286.
Bourcier, T. et al., "Regulation of human corneal epithelial cell proliferation and apoptosis by dexamethasone," Investigative Ophthalmology & Visual Science, 2000, 41(13), 4133-4141.
Buren, J. et al., "Dexamethasone impairs insulin signaling and glucose transport by depletion of insulin receptor substrate-1, phosphatidylinositol 3-kinase protein kinase B in primary cultured rat adipocytes," European Journal of Endocrinology, 2002, 146, 419-429.
Calleja, C. et al., "The antibiotic rifampicin is a nonsteroidal ligand and activator of the human glucocorticoid receptor," Nat. Med., Jan. 1998, 4, 92-96.
Cao, Y et al., Bridging Tendon Defects Using Autologous Tenocyte Engineered Tendon in a Hen Model, Plast. Reconstr. Surg., 2002, 110, 1280-1289.
Chan et al., "Insulin-through the ages: Phylogeny of a growth promoting and metabolic regulatory hormone," American Zoologist, Apr. 2000, accessible at http://www.findarticies.com/p/articles/mi__qa3746/is__200004/ai__n8899929.
Dahlgren et al., "Effects of β-aminopropionitrile on equine tendon metabolism in vitro and on effects of insulin-like growth factor-I on matrix production by equine tenocytes," AJVR, 2001, 62(10), 1557-1562.
Fernandez-Figares, I. et al., "The role of insulin, glucagon, dexamethasone, and leptin in the regulation of ketogenesis and glycogen storage in primary cultures of porcine hepatocytes prepared from 60kg pigs," Domestic Animal Endocrinology, 2004, 27, 125-140.
Ganguly, R. et al., "Absolute requirement of glucocorticoid for expression of the casein gene in the presence of prolactin," Proceedings of the National Academy of Sciences USA, 1980, 77(10), 6003-6006.
Gauger, A. et al., "A low-serum medium for tendon cells: effects of growth factors on tendon cell growth and collagen production," In Vitro Cellular & Developmental Biology, 1985, 21(5), 291-296.
Grandhi, A. et al., "A comparative pharmacological investigation of Ashwagandha and Ginseng," J. Ethnopharmacol., 1994, 44, 131-135.
Kang & Kang, "Ideal Concentration of Growth Factors in Rabbit's Flexor Tendon Culture," Yonsei Med. J., 1999, 40(1), 26-29.
Kuroyanagi & Sato, Allergy, 1966, 15, 67-75.
Marsh, D.G., "Preparation and Properties of 'Allergoids' Derived from Native Pollen Allergens by Mild Formalin Treatment," Int. Arch. Of Allergy and Appl. Immunol., 1971, 41, 199-215.
Schulze-Tanzil, G. et al., "Cultivation of human tenocytes in high-density culture," Histochemistry and Cell Biology, 2004, 122, 219-228.
Tarr, G.E., "Manual Edman Sequencing System," in: Methods of Protein Micro-characterisation, J.E. Silver ed., Humana Press, Clifton, N.J., 155-194 (1986).
Torricelli, P. et al., "Effects of systemic glucocorticoid administration on tenocytes," Biomedicine and Pharmacotherapy, 2006, 60, 380-385.
Wong, M.W.N. et al., "Glucocorticoids suppress proteoglycan production by human tenocytes," Acta Orthopaedica, 2005, 76(6), 927-931.
Youssef, J. et al., "Glucocorticoid-like effects of antihepatocarcinogen Rotenone are mediated via enhanced serum corticosterone levels: Molecular Fitting and Receptor Activation Studies," J. Carcinogenesis, 2003, 2.

*Primary Examiner* — Christian Fronda
(74) *Attorney, Agent, or Firm* — Woodcock Washburn LLP

(57) ABSTRACT

The present invention relates to a method for culturing tenocytes. In particular the present invention relates to a method for culturing tenocytes comprising the step of incubating tenocytes in a culture medium comprising insulin or functional derivative.

14 Claims, 1 Drawing Sheet

SEQUENCE LISTING

<160> NUMBER OF SEQ ID NOS: 6

<210> SEQ ID NO 1
<211> LENGTH: 20
<212> TYPE: DNA
<213> ORGANISM: Homo Sapiens

<400> SEQUENCE: 1
ctcgctcacc accttctctc                      20

-continued

```
<210> SEQ ID NO 2
<211> LENGTH: 20
<212> TYPE: DNA
<213> ORGANISM: Homo sapiens

<400> SEQUENCE: 2
tgttctgaga ggcgtgattg                                              20

<210> SEQ ID NO 3
<211> LENGTH: 20
<212> TYPE: DNA
<213> ORGANISM: Homo sapiens

<400> SEQUENCE: 3
accaacctct tcctgaagcc                                              20

<210> SEQ ID NO 4
<211> LENGTH: 20
<212> TYPE: DNA
<213> ORGANISM: Homo sapiens

<400> SEQUENCE: 4
caccattgag acattttgaa                                              20

<210> SEQ ID NO 5
<211> LENGTH: 20
<212> TYPE: DNA
<213> ORGANISM: Homo sapiens

<400> SEQUENCE: 5
tcaccatctt ccaggagcga                                              20

<210> SEQ ID NO 6
<211> LENGTH: 20
<212> TYPE: DNA
<213> ORGANISM: Homo sapiens

<400> SEQUENCE: 6
cacaatgccg aagtggtcgt                                              20
```

US 7,985,408 B2

TENOCYTE CELL CULTURING METHOD

CROSS-REFERENCE TO RELATED APPLICATIONS

This application is the National Stage of PCT/AU2007/000362, filed Mar. 23, 2007, which claims the benefit of Australian Application No. 2006901495, filed Mar. 23, 2006, both of which are incorporated by reference in their entireties.

FIELD

The present invention relates to a method for culturing tenocytes. In particular the present invention relates to a method for culturing tenocytes to produce a substantially pure culture of tenocytes using a selective medium.

BACKGROUND

Cell culture is a technique having many applications; however some cells, such as tenocytes, hepatocytes, osteoblasts, myoblasts and cardiomyocytes can be difficult and/or slow to culture and/or tend to display an unstable phenotype and dedifferentiate in culture. The use of cultured tenocytes would have application inter alia in the repair of damaged tendons and ligaments.

One common example of damage to a tendon is a tear in the rotator cuff tendon. This commonly results from overhead activity and shows high clinical presentation. Loss of rotator cuff tendon integrity results in impaired strength measurements, and reduced range of motion and function. Although the surgical repair of rotator cuff tendon tears achieve high levels of functional improvement and patient satisfaction, some tendon repairs, especially of large and retracted tears, fail to heal or subsequently re-tear after surgery. Revision surgery for failed rotator cuff repair has very little success compared to primary treatment.

The fundamental principle of tendon repair is to prevent apoptosis of tenocytes and to restore normal tenocytes within the damaged tendon, but this requires the development of phenotypically stable tenocytes cultivated in vitro. However large numbers of tenocytes are required for the regeneration of a tendon or ligament. Moreover, the tenocytes should be of a phenotype as close as possible to that of tenocytes found in the body. Ideally, the cultured tenocytes are autologous for the subject requiring the tendon repair.

Currently, there are no adequate methods for culturing tenocytes to a sufficient degree of uniformity that they can be used to repair tendon or ligament damage. Many of the procedures described in the literature involve the culturing of intact tendons or, at best minced tendons, in the presence of growth factors such as insulin-like growth factors I or II (IGF-I or IGF-II) (see, for example, Dahlgren et al., 2001, *AJVR*, 62(10): 1557-1562; Kang & Kang, 1999, *Yonsei Med. J.*, 40(1): 26-29; Abrahamsson, 1996, *J. Ortho. Res.*, 15: 256-262; Abrahamsson & Lohmander, 1996, *J. Ortho. Res.*, 14: 370-376; Abrahamsson et al., 1991, *Ortho. Res. Soc.*, 9: 495-502 & 503-515; and Anitua et al., 2005, *J. Ortho. Res.*, 23: 281-286). While these methods demonstrate growth enhancement of "tendon-like" or "tendon-derived" cells it is well established that tendons do not solely comprise tenocytes. Indeed, most of the cells in tendons are fibroblasts along with endothelial cells, synovial cells and some chondrocytes. Accordingly, the known methods for culturing tendon cells do not result in pure cultures of tenocytes, but a mixed population of cells comprising fibroblasts, endothelial cells and a small number of tenocytes. It is well-known that tenocytes are slow growing cells and as such are often overgrown by other cells present in culture. This means that the prior art methods for culturing tendon-derived cells generally produce insufficient tenocytes for their use in tissue repair procedures.

Accordingly there is a need for a method for culturing tenocyte cells sufficient to enable their use in tissue repair procedures.

SUMMARY

Accordingly, in a first aspect the invention provides a tenocyte culture medium comprising insulin or functional derivative. In some embodiments the culture medium comprises about 0.00005% to 0.1% w/v insulin or functional derivative. In other embodiments the culture medium comprises about 0.0001% to 0.001% w/v insulin or functional derivative. In still other embodiments the culture medium comprises about 0.0006% w/v insulin or functional derivative.

The culture medium of the first aspect may further comprise a glucocorticoid, such as a synthetic glucocorticoid, or a glucocorticoid-like molecule. In some embodiments the glucocorticoid is betamethasone. The culture medium may comprise about 0.00001% to 0.1% w/v glucocorticoid or a glucocorticoid-like molecule. In some embodiments the culture medium comprises about 0.0001% to 0.001% w/v glucocorticoid or a glucocorticoid-like molecule. In still other embodiments the culture medium comprises about 0.0002% w/v glucocorticoid or a glucocorticoid-like molecule.

In a second aspect the invention provides a tenocyte cell culture medium comprising a glucocorticoid or a glucocorticoid-like molecule. In some embodiments the glucocorticoid is a synthetic glucocorticoid or glucocorticoid-like molecule. In other embodiments the glucocorticoid is betamethasone. The culture medium may comprise about 0.00001% to 0.1% w/v glucocorticoid or a glucocorticoid-like molecule. In some embodiments the culture medium comprises about 0.0001% to 0.001% w/v glucocorticoid or a glucocorticoid-like molecule. In other embodiments the culture medium comprises about 0.0002% w/v glucocorticoid or a glucocorticoid-like molecule.

In some embodiments, the present invention provides a tenocyte culture medium consisting essentially of insulin or functional derivative. In other embodiments, the tenocyte culture medium consists essentially of insulin and a glucocorticoid or a glucocorticoid-like molecule. In these media it will be well appreciated by those skilled in the art that the non-essential ingredients of the culture medium includes, serum, antibiotics and any other typical culture supplements known in the art.

Accordingly, the culture medium of the first and second aspects may further comprise serum, such as fetal bovine serum (FBS). The culture medium may comprise about 15% v/v serum.

The culture medium of the first and second aspects may further comprise an antibiotic. In some embodiments the antibiotic is selected from one or more of the group consisting of ampicillin, carbenicillin, penicillin, amphotericin, nystatin, polymixin-B, gentamycin, kanamycin, neomycin, streptomycin, a tetracycline, a macrolide. linomycin, tiamutin, and chloramphenicol. The culture medium may comprise 1% v/v antibiotic.

The culture medium of the first and second aspects may further comprise L-proline and in some embodiments comprises 0.0006% w/v L-proline.

In a third aspect the invention provides a method of culturing a tenocyte, comprising the step of incubating the tenocyte in a culture medium of the first or second aspects of the invention. In some embodiments the tenocyte is cultured under 10% $CO_2$. In other embodiments the tenocyte is in a 2-D culture. In still other embodiments the tenocyte has been extracted from tendon and/or ligament tissue using trypsin and collagenase.

In some embodiments, the tenocyte culture method of the present invention results in a substantially pure culture of tenocytes (e.g. at least 80%, preferably 90%, more preferably at least 95% of all cells present are tenocytes).

In a fourth aspect the invention provides the use of a tenocyte cultured by a method of the third aspect of the invention for the treatment of a tendon and/or ligament disorder. In some embodiments the tendon disorder is tendinosis. In other embodiments the tendon disorder is a tendon tear.

In a fifth aspect the invention provides the use of a tenocyte cultured by a method of the third aspect of the invention for tendon and/or ligament regeneration.

In a sixth aspect the invention provides the use of a tenocyte cultured by a method of the third aspect of the invention for tendon and/or ligament reconstruction.

In a seventh aspect the invention provides a method of treating a tendon and/or ligament disorder comprising the step of administering to an animal a tenocyte cultured by a method of the third aspect of the invention. In some embodiments the tendon disorder is tendinosis. In other embodiments the tendon disorder is a tendon tear.

In an eighth aspect the invention provides a method of regenerating a tendon and/or ligament, comprising the step of administering to an animal in need thereof a tenocyte cultured by a method of the third aspect of the invention.

In a ninth aspect the invention provides a method of reconstructing a tendon and/or ligament, comprising the step of administering to an animal in need thereof a tenocyte cultured by a method of the third aspect of the invention.

DETAILED DESCRIPTION

Figure 1:
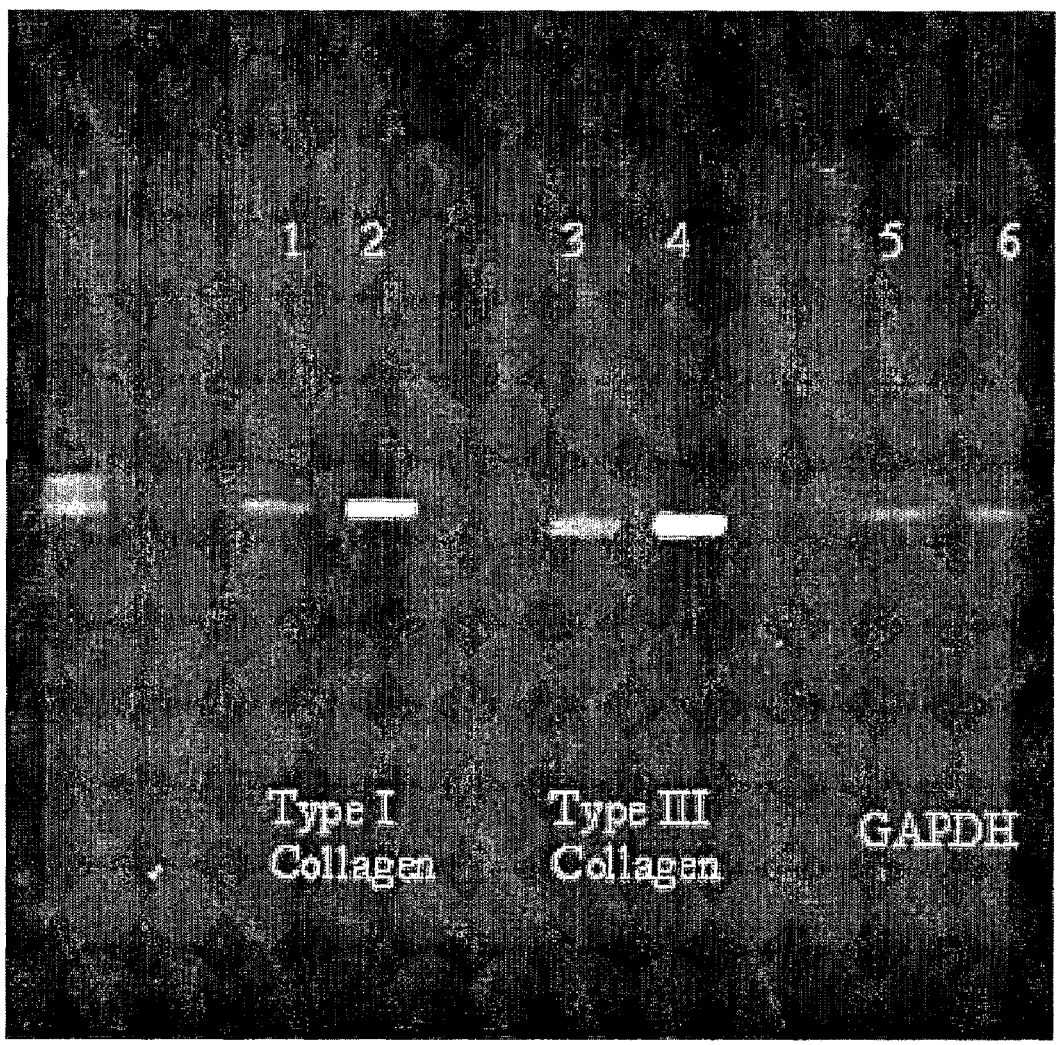
FIG. 1 shows the results of an RT-PCR amplification and illustrates that tenocytes maintain their phenotype in vitro as both collagen I and III bands were detected. Bands 1, 3, and 5 are tendon tissue, whilst bands 2, 4, and 6 are from in vitro tenocyte culture. Bands 1 and 2 represent type I collagen mRNA.

Before describing preferred embodiments in detail, it is to be understood that the terminology used herein is for the purpose of describing particular embodiments of the invention only and is not intended to be limiting.

All publications, patents and patent applications cited herein, whether supra or infra, are hereby incorporated by reference in their entirety. However, publications mentioned herein are cited for the purpose of describing and disclosing the protocols and reagents which are reported in the publications and which might be used in connection with the invention. Nothing herein is to be construed as an admission that the invention is not entitled to antedate such disclosure by virtue of prior invention.

The practice of the present invention will employ, unless otherwise indicated, conventional techniques of tissue dissociation, cell biology, and cell culture which are within the skill of the art. Such techniques are described in the literature. See, for example, Immunochemical Methods in Cell and Molecular Biology (Mayer and Walker, eds., Academic Press, London, 1987); Molecular Biology of the Cell (Alberts et al, Garland Science, New York, 2000); Kruse & Patterson, eds., Tissue Culture (Academic Press, 1977); and Culture Of Animal Cells (R. I. Freshney, Alan R. Liss, Inc., 1987).

It must be noted that as used herein and in the appended claims, the singular forms "a," "an," and "the" include plural reference unless the context clearly dictates otherwise. Thus, for example, a reference to "a cell" includes a plurality of cells and "a molecule" refers to a plurality of molecules, and so forth.

Unless defined otherwise, all technical and scientific terms used herein have the same meanings as commonly understood by one of ordinary skill in the art to which this invention belongs.

In the description that follows, if there is no instruction, it will be appreciated that cell culture techniques are well-known in this field and any such technique may be adopted.

Although any materials and methods similar or equivalent to those described herein can be used to practice or test the present invention, the preferred materials and methods are now described.

In one embodiment, the present invention provides a tenocyte cell culture medium. The terms "tenocyte cell culture medium" and "culture medium" are used herein interchangeably and refers to a nutrient solution used for selectively growing tenocytes cells. While the culture medium of the present invention comprises specific components as described supra and infra other, non-essential ingredients, are also included and these will depend upon the animal source of the tenocytes or tenocyte-containing tissue and the culture conditions used e.g. cell density and/or end use. The tenocyte culture medium usually comprises a mixture of organic and inorganic materials and typically provides at least one component from one or more of the following categories:

1) an energy source, usually in the form of a carbohydrate such as glucose;
2) all essential amino acids, and usually the basic set of twenty amino acids plus cysteine;
3) vitamins and/or other organic compounds required at low concentrations;
4) free fatty acids; and
5) trace elements, where trace elements are defined as inorganic compounds or naturally occurring elements that are typically required at very low concentrations, usually in the micromolar range.

The culture medium may optionally be supplemented with one or more components from any of the following categories:

1) hormones and other growth factors, for example, transferrin and epidermal growth factor;
2) salts and buffers, for example, calcium, magnesium, and phosphate;
3) nucleosides and bases such as, adenosine and thymidine, hypoxanthine; and
4) protein and tissue hydrolysates.

Typically the culture medium comprises a commercially available culture medium, such as Basal Media Eagle (EME), BGJb Medium, Brinster's BMOC-3 Medium, CMRL Medium, CO2-Independent Medium, Dulbecco's Modified Eagle Media (D-MEM), F-10 Nutrient Mixtures, F-12 Nutrient Mixtures, Glasgow Minimum Essential Media, Improved MEM Zn++ Option (Richter's Modification), Iscove's Modified Dulbecco's Media, Leibovitz's L-15 Media, McCoy's 5A Media (modified), MCDB 131 Medium, Medium NCTC-109, Minimum Essential Media (MEM), Modified Eagle Medium (MEM), Opti-MEM® I Reduced Serum Media, RPMI Media 1640, Waymouth's MB 752/1 Media, Williams Media E. and Medium 199.

The tenocyte culture medium of the invention comprises insulin or a functional derivative thereof. Insulin is a hormone which, in its naturally-occurring form, is produced by the pancreas. However, the insulin used in the medium of the invention may by synthetic, such as recombinant insulin, or naturally occurring.

An "functional derivative" of insulin is a molecule such as those described by Chan et al., 2000, "Insulin-through the ages: Phylogeny of a growth promoting and metabolic regulatory hormone" (American Zoologist; accessible at http://www.findarticles.com/p/articles/mi_qa3746/is_200004/ai_n8899929 having the activity of insulin, namely, the ability to culture tenocytes and includes biologically active fragments, variants, and derivatives of insulin.

In some embodiment, a "functional derivative" of insulin or a fragment or variant thereof has one or several amino acid residues substituted by naturally occurring or synthetic amino acid homologues of the 20 standard amino acids. Examples of such homologues are 4-hydroxyproline, 5-hydroxylysine, 3-methylhistidine, homoserine, ornithine, β-alanine and 4-aminobutanoic acid, β-alanine, norleucine, norvaline, hydroxyproline, thyroxine, gamma-amino butyric acid, homoserine, citrulline, and the like.

A functional derivative of insulin can be prepared using polyethylene glycol (PEG) according to the method of Sehon and co-workers (Wie et al., supra) to produce an insulin molecule conjugated with PEG. In addition, PEG can be added during chemical synthesis of insulin. Other methods of preparing a derivative of insulin or a fragment thereof include reduction/alkylation (Tarr, Methods of Protein Micro-characterisation, J. E. Silver ed., Humana Press, Clifton N.J. 155-194 (1986)); acylation (Tarr, supra); chemical coupling to an appropriate carrier (Mishell and Shiigi, eds, Selected Methods in Cellular Immunology, W H Freeman, San Francisco, Calif. (1980), U.S. Pat. No. 4,939,239; or mild formalin treatment (Marsh, 1971, *Int. Arch. of Allergy and Appl. Immunol.*, 41:199-215).

It should be noted that the term "functional derivative" does not include molecules such as insulin-like growth factor I or II.

The insulin or functional derivative may be incorporated into the culture medium prior to adding the tenocyte cells to be cultured. Alternatively, the insulin or functional derivative may be added to the medium throughout the culture, for example, by culturing the cells in the presence of a cell feeder layer, such as beta cells, which secrete insulin or a functional derivative.

As used herein a "fragment" is a portion of the insulin protein which retains the function of insulin and in particular, the ability to support the growth of tenocyte cells in culture. A fragment of insulin can be at least about 10 amino acid residues in length, preferably about 10-16 amino acid residues in length, and more preferably about 10-20 amino acid residues in length.

A "variant" of insulin is an insulin molecule that has one or more substitutions such that the secondary conformation thereof remains unchanged. Examples of such conservative substitutions include amino acids having substantially the same hydrophobicity, size and charge as the original amino acid residue. Such substitutions are generally well known to those skilled in the art of protein or peptide chemistry. For example, conservative substitutions include proline for glycine and vice versa; alanine or valine for glycine and vice versa; isoleucine for leucine and vice versa; histidine for lysine and vice versa; threonine for cysteine and vice versa; glutamine for asparagine and vice versa; and arginine for glutamate and vice versa.

Another example of a variant of insulin is one in which the cysteine residues have been substituted to minimise dimerisation via disulfide linkages. Preferably the cysteine residues are substituted with alanine, serine, threonine, leucine or glutamic acid residues. In addition, amino acid side chains of insulin or fragment or derivative thereof can be chemically modified. Another modification is cyclisation of the insulin.

The amount of insulin or functional derivative in the medium of the invention is typically in the range of about 0.00005% to about 0.1% w/v. In some embodiments the insulin or functional derivative is in the range of about 0.0005% to about 0.01% w/v. In other embodiments the insulin or functional derivative is in the range of about 0.0001% to about 0.001% w/v. In still other embodiments the insulin or functional derivative is about 0.0006% w/v.

In some embodiments the culture medium comprises a glucocorticoid, or a glucocorticoid-like molecule. Glucocorticoids are a class of steroid hormones characterised by an ability to bind to the cortisol receptor and trigger similar effects, such as affecting metabolism or anti-inflammatory or immunosuppressive effects. Glucocorticoids may be naturally-occurring (hormones) or synthetic (drugs).

Examples of synthetic glucocorticoids suitable for use in the invention include hydrocortisone, cortisone acetate, prednisone, prednisolone, methylprednisolone, dexamethasone, betamethasone, triamcinolone, beclometasone, fludrocortisones acetate, deoxycorticosterone acetate (DOCA), and aldosterone.

A "glucocorticoid-like" molecule may be any molecule having an activity of a glucocorticoid, namely the ability to culture tenocytes. Examples of glucocorticoid-like molecules suitable for use in the invention include the antihepatocarcinogen, Rotenone (Youssef et al., 2003, *J. Carcinogenesis* 2:2), Rifampcin (Calleja et al., 1998, *Nat. Med.*, 4:92-96), Glycyrrhizin (a component of licorice) (Kuroyanagi & Sato, 1966, *Allergy*, 15:67-75), and Withanolides (from the herb *Withanthia somnifera*) (Grandhi et al., 1994, *J. Ethnopharmacol.*, 44:131-135).

In some embodiments the glucocorticoid is betamethasone. Betamethasone is a synthetic glucocorticoid having the formula $C_{22}H_{29}FO_5$.

The amount of glucocorticoid or glucocorticoid-like molecule in the medium of the invention is typically in the range of about 0.00001% to about 0.1% w/v. In some embodiments the glucocorticoid or glucocorticoid-like molecule is in the range of about 0.0001% to about 0.001% w/v. In other embodiments the glucocorticoid or glucocorticoid-like molecule is in the range of about 0.0002% to about 0.001% w/v.

The medium may further comprise serum. The serum may be from any animal, but typically is bovine serum. In some embodiments the serum is fetal bovine serum. The amount of serum in the medium may be between about 1% to 30% v/v. In some embodiments the amount of serum in the medium is between about 5% to 20% v/v. In other embodiments the amount of serum in the medium is between about 10% to 15% v/v.

The medium may further comprise one or more antibiotics. An antibiotic is a natural or synthetic substance which kills or inhibits the growth of a microorganism. Examples of antibiotics suitable for use in a medium of the invention include ampicillin, carbenicillin, penicillin, amphotericin, nystatin, polymixin-B, gentamycin, kanamycin, neomycin, streptomycin, a tetracycline, a macrolide, linomycin, tiamutin, and chloramphenicol.

The medium may comprise between about 0.0010% and 5% v/v antibiotic. In some embodiments the amount of antibiotic is between about 0.01% and 0.05% v/v antibiotic. In other embodiments the amount of antibiotic is about 1% v/v.

L-proline is the L-stereoisomer of proline, one of the 20 amino acids commonly found in animal proteins. Only the L-stereoisomer appears in mammalian proteins.

The pH of the medium may be any pH which allows growth of the cells to be cultured. In some embodiments the pH of the culture medium is about 9.0 to about 3.0. In other embodiments the pH is about 5.0 to 8.0. In still other embodiments the pH is about 7.0 to 7.5. In still other embodiments the pH is about 7.2.

The culture medium of the invention may be prepared by any means known in the art. For example, the medium may be prepared by dissolving the dry ingredients in water and adjusting the liquid to the desired pH. This may be sterilised by one of numerous methods such as filtration or irradiation. Any sterile liquid ingredients may then be added to the medium.

Tenocyte cells to be cultured or tissue-containing tenocytes can then be added to the culture medium. The term "tenocyte" as used herein refers to the spindle-shaped, fibroblast-like cells that are found in tendons of animals. Tenocytes typically have elongated nuclei and thin cytoplasm and are often found sitting on collagen fibres in tendons. Tenocytes can often be identified on the basis that they produce collagen type I and express the marker "scleraxis". Tenocyte cells can be isolated from any tenocyte-containing tissue in a variety of ways, all which are known to one skilled in the art. In some embodiments, tenocyte cells can be isolated from a biopsy material by conventional methods. For example, an animal requiring treatment or regeneration of a tendon can have a biopsy taken from any tendon in the body. Such tendons include, but are not limited to, tendon of flexor carpi radialis and the calcaneus tendon.

In some embodiments, the tenocyte cells or tenocyte-containing tissue are "autologous cells or tissue" i.e. tenocyte cells or tissue originating from the body of the animal subject to be treated.

As used herein an "animal" means any animal, such as a human or a mammal of economical importance and/or social importance to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, e.g., poultry, such as turkeys, chickens, ducks, geese, guinea fowl, and the like, as they are also of economical importance to humans. Thus, provided is the treatment of livestock, including, but not limited to, domesticated swine (pigs and hogs), ruminants, horses, poultry, and the like. The term does not denote a particular age. Thus, both adult and newborn subjects are intended to be covered.

Tenocytes can be harvested or isolated from any tenocyte-containing tissue e.g. tendons. A tendon is the tissue which connects muscle to bone in an animal. The tendon may be from any anatomical site of an animal and may be a rotator cuff tendon, supraspinatus tendon, subcapularis tendon, pectroalis major tendon, peroneal tendon, achille's tendon, tibialis anterior tendon, anterior cruciate ligament, posterior cruciate ligament, hamstring tendon, lateral ligament, medial ligament, patella tendon, biceps tendon, and triceps tendon.

In some embodiments, tendon tissues, which have been isolated by biopsy, are washed and minced to form explants which can be grown in cell culture to yield free tenocytes. In some embodiments, the minced tissue is subjected to enzymatic digestion and/or subjected to agents such as ethylenediaminetetraacetic acid (EDTA) that bind or chelates $Ca^{2+}$ on which cell-cell adhesion depends. Examples of enzymes suitable for use include one or more of collagenase, trypsin, and proteases.

In one preferred method, minced tendon tissue of no larger than 1 mm is incubated in the presence of 2.5% w/v trypsin and 5.5% w/v collagenase in standard tissue culture medium without phenol red for at least 3 hours at 37° C. in a 5% $CO_2$.

In some embodiments, after enzymatic digestion, the cells from the biopsy material are isolated by centrifuging the biopsy solution, and washing the resulting pellet with cell growth medium. Alternatively, the tenocytes may then be separated from the other components of the tendon by filtration through, for example, a mesh such as a sterile 150 micron nylon mesh. Another approach is based on the tendency of some cell types to adhere strongly to plastic or glass, which allows them to be separated from components of a tendon which do not adhere as strongly.

Alternatively, the cells may be separated from other components of the tendon using antibodies that specifically bind to the cell, for example using antibodies conjugated to a matrix or coupled to a fluorescent dye which can then be separated by fluorescent-activated cell sorting (FACS).

The cells may then be added to the culture medium of the present invention and incubated under suitable conditions. In some embodiments, following isolation, the cells are cultured for about 3 days to about five weeks, at 37° C. in a 5% $CO_2$ atmosphere. The time period for cell culturing can, of course, vary.

As described supra, the culture medium of the present invention comprises insulin or functional derivative and/or glucocorticoid or a glucocorticoid-like molecule. Tenocytes are typically very difficult to grow in cell culture and tend to be unstable and dedifferentiate. However, the inventor has found that insulin in particular enables tenocytes to grow more stably and establish in culture even in the presence of other cells including chondrocytes, fibroblasts and the like. Accordingly, as long as insulin is present in the medium of the present invention then tenocytes can be selectively expended. As described elsewhere insulin may be added to the medium exogenously. Alternatively, the insulin can be produced naturally by co-culturing the tenocytes with feeder cells capable of secreting insulin into the medium.

Thus, in the present context, "feeder cells" or "feeders" are cells that are capable of excreting insulin such that the co-cultured tenocyte cells are able to grow as required by the present invention. Whether the tenocyte cells are grown essentially feeder-free or in the presence of feeder cells, in some embodiments, the tenocyte cells reach a cell density that requires them to be split into one or more sub-cultures. Each round of subculturing is referred to as a passage. When tenocyte cells are subcultured, they are referred to as having been passaged. A specific population of tenocyte cells is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but not limited to the seeding density, substrate, medium, growth conditions, and time between passaging.

Preferably, the methods of the present invention produce a culture or subculture of tenocyte cells that are substantially pure. The term "substantially pure" as used herein means that the tenocytes in culture are the predominate cells and other contaminating cells such as fibroblasts, chondrocytes and the like are in lesser number. Preferably, at least 80% of the cells present in culture are tenocytes, more preferably 90%, even more preferably at least 95% of all cells present are tenocytes.

Once a sufficient number or volume of tenocytes have been obtained they can be banked or stored by standard techniques. For example, tenocytes cells can be conveniently stored by cryopreservation at −180° C. The tenocyte cells of the invention are readily cryopreserved under a variety of conditions such as are known in the art.

Importantly, during the culturing phase or following passage or after cryopreservation it is preferable that the phenotype of the tenocyte cells is assessed. There are numerous methods of assessing the phenotype of cells subjected to cell culture. One method is to assess the morphology of the cultured cells. For example, tenocytes are spindle-shaped cells with elongated nuclei and thin cytoplasm.

Another method of assessing the phenotype of a cultured cell is to determine whether the cell expresses markers specific for the cell type. For example, tenocytes express a transcription factor, scleraxis, which is a highly specific marker for all the connective tissues that mediate attachment of muscle to bone. Tenocytes also express differentiation markers like collagen type-I, collagen type-III, and decorin.

It will be apparent to person skilled in the art that the tenocyte cells of the present invention may be incubated in a monolayer or in a 3-dimensional culture depending upon their end use. A "monolayer" is a single layer of cells (2-dimensional). A 3-dimensional culture refers to a culture which has a depth, width, and height, such as a culture growing on a matrix or scaffold.

Thus, the present invention also contemplates compositions that include tenocyte cells, preferably autologous tenocyte cells, seeded onto a support matrix or scaffold for use in tissue repair and/or regeneration. By "seeding" is meant that tenocyte cells are brought into contact with a support matrix or scaffold, and adhere (with or without an adhesive) to the support matrix for a period of time prior to transplantation.

In some embodiments of the invention, the cells are retained only on one surface or an edge of, or to a specified depth (as described herein) of the support matrix, i.e., the cells are adhered to one surface or are adjacent the support matrix, such as described in U.S. Publication No. 20020173806, hereby incorporated by reference in its entirety.

In the present invention, uniform seeding is preferable. It is believed that the number of tenocyte cells seeded does not limit the final tissue produced, however optimal seeding may increase the rate of generation. Optimal seeding amounts will depend on the specific culture conditions. In some embodiments, the matrix is seeded with from about 0.05 to about 5 times the physiological cell density of a native tissue type, i.e., in tendon. In another embodiment, the cell density can be less than about $1\times10^5$ to $1\times10^8$ cells, or more, per ml, typically about $1\times10^6$ cells per ml.

The support matrix or scaffold can be in any form suitable for tenocyte or cell adherence with or without an adhesive. By way of example and not limitation, the support matrix or scaffold can be in the form of a membrane, microbead, fleece, thread, or gel, and/or mixtures thereof. The support matrix or scaffold can be made out of any material that has the physical or mechanical attributes required for implantation, such as acting as a hemostatic barrier. A hemostatic barrier inhibits penetration of adjunct cells and tissue into the treated defect area.

The support matrix or scaffold is preferably made of a semi-permeable material which may include cross-linked or uncross-linked collagen, preferably type I in combination with type III, or type II. The support matrix or scaffold may also include polypeptides or proteins obtained from natural sources or by synthesis, such as hyaluronic acid, small intestine submucosa (SIS), peritoneum, pericardium, polylactic acids and related acids, blood (i.e., which is a circulating tissue including a fluid portion (plasma) with suspended formed elements (red blood cells, white blood cells, platelets), or other material which is bioresorbable. Bioabsorbable polymers, such as elastin, fibrin, laminin and fibronectin are also useful in the present invention. Support matrix or scaffold materials as described in US Publication No. 20020173806, herein incorporated by reference in its entirety, are also useful in the present invention.

In addition, the support matrix or scaffold preferably is initially (i.e., before contact with the cells to be transplanted) free of intact cells and is resorbable within the animal subject. The support matrix or scaffold may have one or several surfaces, such as a porous surface, a dense surface, or a combination of both. The support matrix may also include semi-permeable, impermeable, or fully permeable surfaces. Support matrices having a porous surface are described, for example, in U.S. Pat. No. 6,569,172, which is incorporated herein by reference in its entirety.

The support matrix is autologous or allogeneic. In some embodiments, a suitable autologous support matrix is formed from blood, as exemplified in U.S. Pat. No. 6,368,298, issued to Berretta, et al. on Apr. 9, 2002, herein incorporated by reference in its entirety.

A suitable support matrix or scaffold will be a solid, semi-solid, gel, or gel-like scaffold characterized by being able to hold a stable form for a period of time to enable the adherence and/or growth of cells thereon, both before transplant and after transplant, and to provide a system similar to the natural environment of the cells to optimize cell growth. Examples of suitable support matrices are disclosed in US Publication No. 20020173806, which is hereby incorporated by reference in its entirety.

In some embodiments, the support matrix or scaffold and/or cells, either individually or in combination, may be combined with an adhesive (e.g., a biocompatible glue such as fibrin glue which may be autologous or allogeneic) or physical or mechanical retention means such a resorbable pin to assist in retaining the repair structures according to the present invention in or over the site of transplantation.

Additional examples of suitable support matrixes or scaffolds for growth of tenocytes include Vitrogen™, a collagen-containing solution which gels to form a cell-populated matrix, and the connective-tissue scaffolds of Hwang (US patent application no. 20040267362), Kladaki et al (US patent application no. 20050177249), Giannetti (US patent application no. 20040037812) and Binette et al (US patent application no. 20040078077). Suitable scaffolds, such as that of Hwang, are ideally able to not only support tenocytes growth but are also able to be transferred into an animal to replace damaged tendon or ligament tissue.

The support matrix or scaffold can be cut or formed into any regular or irregular shape. In a preferred embodiment, the support matrix or scaffold can be cut to correspond to the shape of the defect. The support matrix can be flat, round and/or cylindrical in shape. The shape of the support matrix can also be moulded to fit the shape of a particular tissue defect. If the support matrix is a fibrous material, or has the characteristics of a fibre, the support matrix can be woven into a desired shape. Alternatively, the support matrix can be a gel, gel-like, or non-woven material.

In some embodiments, a support matrix or scaffold of the present invention can be seeded with multiple cell types and have different cell types on and/or in and/or throughout and/or adjacent to different portions of the support matrix or scaffold. By way of example, one portion of the support matrix may include a first cell type (e.g., tenocytes) and another portion of the matrix may include a second cell type (e.g., muscle cells).

By way of further example, if the matrix or support is disc shaped, having two sides and an edge, a first side can include a first cell type (e.g., tenocyte) thereon and the second side or edge can include a second cell type (e.g., muscle cells) thereon.

In another embodiment, two or more support matrices or supports can be in contact with each other. In such an embodiment, a first support matrix can be in contact with a second support matrix either before, during or after either support matrix is contacted with one or more cell types.

After the tenocytes or other cells are seeded onto the support matrix or scaffold, the support matrix or scaffold and the cells are transplanted into the tissue defect, with cells facing the surface to be treated. In one embodiment, a covering patch is secured (e.g., In some embodiments, a covering patch serves to cover the defect to further prevent infiltration of undesired materials, such as fibroblasts or macrophages, from the surrounding environment. In one embodiment, the covering patch may be any of the support matrices described herein, and/or can include collagen (type I/III), hyaluronic acid, fibrin and polylactic acid. Preferably, the covering patch is cell-free and resorbable, and may be semi-permeable.

In one embodiment, the support matrix or scaffold and cells are injectable to the site of transplantation, with or without an adhesive or glue.

A seeded support matrix or scaffold of the present invention can also include various pharmacological actives including but not limited to antimicrobials, antivirals, antibiotics, growth factors suitable to the type of tissue to be regenerated and/or repaired, blood clotting modulators such as heparin and the like, as well as mixtures and composite layers thereof can be added to the biocompatible biodegradable support matrix material, prior to impregnation into the support matrix.

A seeded support matrix or scaffold of the present invention can also include growth factors such as autologous and non-autologous growth factors suitable to the type of tissue to be regenerated and/or repaired, including but not limited to transforming growth factor (such as TGF-beta-3), bone morphogenetic protein (such as BMP-2), PTHrP, osteoprotegrin (OPG), Indian Hedgehog, RANKL, and insulin-like growth factor (IgF1), as described in US Publication No. 20030144197, the entire content of which is hereby incorporated by reference.

As noted supra, the present invention can also include biocompatible glue in contact with a substrate and/or biodegradable material and/or cells. Such biocompatible glues or adhesives can include an organic fibrin glue (e.g., Tisseel™ fibrin based adhesive available from Baxter, Austria, or a fibrin glue prepared in the surgical theatre using autologous blood samples).

As described supra, cultured tenocytes may be used for tendon and/or ligament regeneration and reconstruction. The regeneration or reconstruction of the tendon and/or ligament may be partial or complete and may provide partial or complete recovery of range of motion of the affected tendon or ligament. For example, tendon defects may be repaired using tenocytes cultured according to the invention and a method as described by Cao et al 2002 (Plast Reconstr Surg 110:1280-1289) or Curtis et al 2005 (European Cells and Materials 9:50-57).

The cultured tenocyte cells may be used for the regeneration and/or reconstruction of any tendon and/or ligament. For example, the shoulder, elbow, knee, and ankle joints are the most commonly affected by tendon or ligament injuries. Hence the cultured cells may be used inter alia for the regeneration or reconstruction of the rotator cuff tendon, supraspinatus tendon, subcapularis tendon, pectroalis major tendon, peroneal tendon, achille's tendon, tibialis anterior tendon, anterior cruciate ligament, posterior cruciate ligament, hamstring tendon, lateral ligament, medial ligament, patella tendon, biceps tendon, and triceps tendon.

The cultured tenocytes may also be used in the treatment or prevention of a tendon or ligament disorder.

"Treating" or "treatment" or grammatical equivalents as used herein covers any treatment of a tendon or ligament disorder in an animal subject, preferably a human, and includes: (a) preventing the tendon or ligament disorder from occurring in a subject that may be predisposed to the disorder, but has not yet been diagnosed as having it; (b) inhibiting the tendon or ligament disorder, i.e., arresting its development; or (c) relieving or ameliorating the symptoms of the tendon or ligament, i.e., cause regression of the symptoms of the disorder. The effect may be prophylactic in terms of completely or partially preventing the disorder or sign or symptom thereof, and/or may be therapeutic in terms of a partial or complete cure of the disorder.

A "disorder" refers to an abnormal state, such as structure or function, of a part of a body. Therefore a tendon or ligament disorder refers, for example, to an abnormal structure or function of the tendon or ligament.

Examples of tendon disorders include tendinosis and tendonitis.

"Tendinosis" is a term referring to intratendinous degeneration of a tendon due to atrophy (aging, microtrauma, vascular compromise). Histologically there is a non-inflammatory intratendinous collagen degeneration with fiber disorientation, hypocelluarity, scattered vascular ingrowth, and occasional local necrosis or calcification. Clinically there is often a palpable tendon nodule that can be asymptomatic, but may also be point tender. There is no swelling of a tendon sheath.

"Tendonitis" refers to a strain or tear of a tendon and is a symptomatic degeneration of the tendon with vascular disruption and inflammatory repair response. The symptoms are inflammatory. Depending on the stage of tendonitis (acute—less than two weeks, subacute—four to six weeks, and chronic—over six weeks) there may be a hematoma, or atrophy-related cell necrosis. Histologically there are three recognized subgroups: 1) purely inflammatory with acute hemorrhage and tear; 2) inflammation superimposed upon pre-existing degeneration; and 3) calcification and tendinosis changes in chronic conditions.

By "comprising" is meant including, but not limited to, whatever follows the word comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The invention will now be further described by way of reference only to the following non-limiting examples. It should be understood, however, that the examples following are illustrative only, and should not be taken in any way as a restriction on the generality of the invention described above. In particular, while the invention is described in detail in relation to the use of insulin, it will be clearly understood that the findings herein are not limited to insulin per se, but also encompasses the derivatives of insulin described supra.

EXAMPLE 1

Harvest of Tendon Tissue for CultivatiON 50 g to 100 g of normal tendon tissue was harvested from the patellae tendon of a human and a horse by a needle biopsy. The tissue was stored in phenol red free 199 medium (Invitrogen) containing 10% v/v fetal bovine serum (FBS) for not more than 72 hours at room temperature.

The tissue was washed with 199 medium and minced into a size not larger than 1 mm and digested in trypsin 2.5% w/v and collagenase 5.5% w/v in 199 medium without phenol red for at least 3 hours at 37° C. in a 5% $CO_2$ incubator.

The tendon digest was passed through a 45 µm size filter to separate the tenocytes from the remainder of the tendon digest. The tenocytes were then used for cell counts and seeded into a 25 $cm^2$ flask for cultivation.

EXAMPLE 2

Culture of Tenocytes

Tenocytes prepared in Example 1 were placed into a culture flask at density between $10^3$ to $10^4$ cells/ml in a dish containing culture medium. The culture medium contained Dulbecco's Modified Eagle Medium (DMEM) (Invitrogene), 15% v/v fetal bovine serum, 0.0006% w/v insulin, 0.0002% w/v betamethasone, 0.5% w/v penicillin, 0.5% w/v streptomycin, and 0.6% L-proline at pH 7.0. The cells were incubated under 5% $CO_2$ at 37° C. The culture medium was changed every third day for 3 to 5 weeks until cells reach the maximum cell numbers at the fifth passage, typically $20 \times 10^7$ cells.

EXAMPLE 3

Characterisation of Human Tenocytes

The expression of tenocytes markers, type-I and type-III collagen mRNA, by the tenocytes cultured under the conditions described in Example 2 was examined to confirm whether the tenocytes maintained their biosynthetic ability in vitro.

Total RNA was extracted from both tendon tissue (control) and tenocytes cultured under the conditions described in Example 2 using an RNAeasy Mini Kit (QIAGEN Australia). RT-PCR was performed to generate and amplify type-I and type-III collagen cDNA as well as DNA from the housekeeping gene, GAPDH. The PCR amplification was performed using the following primer pairs:

Type-I Collagen
Sense

5' CTCGCTCACCACCTTCTCTC 3'    (SEQ ID NO: 1)

Antisense

5' TGTTCTGAGAGGCGTGATTG 3'    (SEQ ID NO: 2)

To produce a product size of 464 bp.
Type-III Collagen
Sense

5' ACCAACCTCTTCCTGAAGCC 3'    (SEQ ID NO: 3)

Antisense

5' CACCATTGAGACATTTTGAA 3'    (SEQ ID NO: 4)

To produce a product size of 254 bp.
Human Glyceraldehyde-3-Phosphate Dehydrogenase (GAPDH)
Sense

5' TCACCATCTTCCAGGAGCGA 3'    (SEQ ID NO: 5)

Antisense

5' CACAATGCCGAAGTGGTCGT 3'    (SEQ ID NO: 6)

To produce a product size of 293 bp.

30 cycles of PCR were performed in a thermocycler under standard conditions, except that 40 second annealing times were used and hybridisation using the Type I and III collagen primers were conducted at 60° C. and the GAPDH primers at 62° C.

The PCR reactions were analysed by electrophoresis and the results are shown in FIG. 1. It can be seen that the tenocytes cultured in a medium of the invention express type-I and type-III collagen mRNA, as does tendon tissue.

The invention claimed is:

1. A tenocyte culture medium comprising insulin and betamethasone.

2. The tenocyte culture medium of claim 1, which comprises about 0.00005% to about 0.1% w/v insulin.

3. The tenocyte culture medium of claim 1, which comprises about 0.0001% to about 0.001% w/v insulin.

4. The tenocyte culture medium of claim 1, which comprises about 0.0006% w/v insulin.

5. The tenocyte culture medium of claim 1, which comprises about 0.00001% to about 0.1% w/v betamethasone.

6. A method of culturing a tenocyte, comprising the step of incubating a tenocyte or tissue containing a tenocyte in the culture medium of claim 1.

7. A method for producing a culture of tenocytes comprising the steps of:
   (i) isolating a tenocyte-containing tissue, washing and mincing same to form explants; and
   (ii) culturing said explants in the presence of a tenocyte culture medium comprising insulin and betamethasone to yield free tenocytes;
   wherein at least 90% of cells present in the culture are tenocytes.

8. The method of claim 7, wherein at least 95% of total cells present in the culture are tenocytes.

9. The tenocyte culture medium of claim 1, which further comprises serum, one or more antibiotics, L-proline or combinations thereof.

10. The tenocyte culture medium of claim 9, wherein the serum is fetal bovine serum.

11. The tenocyte culture medium of claim 9, wherein the antibiotic is selected from one or more of the group consisting of ampicillin, carbenicillin, penicillin, amphotericin, nystatin, polymixin-B, gentamycin, kanarnycin, neomycin, streptomycin, a tetracycline, a macrolide, linomycin, tiamutin, and chloramphenicol.

12. The method of claim 7, wherein the tenocyte-containing tissue is tendon tissue.

13. The method of claim 7, wherein the tenocyte-containing tissue is minced to no larger than 1 mm and is incubated in the presence of 2.5% w/v trypsin and 5.5% w/v collagenase.

14. A tenocyte seeded support matrix comprising a support matrix and a substantially pure culture of tenocytes; where said tenocytes are produced by the method of claim 7 and wherein said tenocytes are seeded onto said support matrix until said tenocytes adhere to the support matrix.

* * * * *